(12) United States Patent
Bailey et al.

(10) Patent No.: US 9,291,635 B2
(45) Date of Patent: Mar. 22, 2016

(54) PROCESS ANALYTIC INSTRUMENT WITH MULTI-TUBE CONNECTION

(71) Applicant: Rosemount Analytical Inc., Houston, TX (US)

(72) Inventors: Edward J. Bailey, Cypress, TX (US); Jason P. Pratt, Cypress, TX (US)

(73) Assignee: Rosemount Analytical Inc., Houston, TX (US)

( * ) Notice: Subject to any disclaimer, the term of this patent is extended or adjusted under 35 U.S.C. 154(b) by 187 days.

(21) Appl. No.: 13/653,572

(22) Filed: Oct. 17, 2012

(65) Prior Publication Data

US 2013/0098140 A1 Apr. 25, 2013

Related U.S. Application Data

(60) Provisional application No. 61/549,427, filed on Oct. 20, 2011.

(51) Int. Cl.
G01N 35/10 (2006.01)
G01N 30/16 (2006.01)
G01N 33/00 (2006.01)

(52) U.S. Cl.
CPC ............ *G01N 35/1074* (2013.01); *G01N 30/16* (2013.01); *G01N 33/0009* (2013.01); *G01N 35/1095* (2013.01)

(58) Field of Classification Search
CPC ................ G01N 2001/002; G01N 2030/8881; G01N 35/1074; G01N 35/1095
See application file for complete search history.

(56) References Cited

U.S. PATENT DOCUMENTS

| 4,088,436 A | 5/1978 | Alferes ............................ 431/21 |
| 4,302,136 A * | 11/1981 | Abe et al. ...................... 411/158 |
| 5,287,746 A | 2/1994 | Broden |
| 5,746,976 A | 5/1998 | Yamada et al. .................. 422/62 |

(Continued)

FOREIGN PATENT DOCUMENTS

| CN | 1077531 | 10/1993 |
| CN | 2366668 Y | 3/2000 |

OTHER PUBLICATIONS

International Search Report and Written Opinion from the corresponding International application No. PCT/US2012/060517 dated Jan. 18, 2013.

(Continued)

*Primary Examiner* — Paul West
(74) *Attorney, Agent, or Firm* — Christopher R. Christenson; Kelly, Holt & Christenson, PLLC

(57) ABSTRACT

A process analytic instrument includes an analytical module configured to analyze a process fluid and a removable tube carrier coupled to the analytical module. The analytical module has a plurality of inlet ports in a sealing surface. The removable tube carrier has an end with a plurality of apertures aligned with the plurality of inlet ports of sealing surface of the analytical module. The removable tube carrier fluidically couples a plurality of tubes to the analytical module when the end of the removable tube carrier is biased into the sealing surface of the analytical module.

14 Claims, 3 Drawing Sheets

(56) References Cited

U.S. PATENT DOCUMENTS

| | | | |
|---|---|---|---|
| 6,029,499 A * | 2/2000 | Sittler et al. | 73/23.42 |
| 6,212,958 B1 | 4/2001 | Conley | |
| 7,014,222 B1 | 3/2006 | Poppe | 285/332.1 |
| 7,150,194 B2 | 12/2006 | Pepperling et al. | |
| 7,681,456 B2 | 3/2010 | Hausler | |
| 2002/0069758 A1 | 6/2002 | Burban et al. | |
| 2004/0170531 A1 | 9/2004 | Mueller | 422/89 |
| 2005/0118068 A1 | 6/2005 | Kahl | 422/100 |
| 2006/0042686 A1* | 3/2006 | Gamache et al. | 137/51 |
| 2008/0072976 A1* | 3/2008 | Bailey et al. | 137/599.01 |

OTHER PUBLICATIONS

First Office Action from counterpart Chinese patent application No. 201280003692.4, issuing date Apr. 23, 2014. 19 pages.

Second Office Action from Chinese Counterpart Patent Application No. 201280003692.4, issuing date: Jan. 15, 2015, 14 pages with English Translation.

Third Office Action from Chinese Patent Application No. 201280003692.4. dated Jul. 14, 2015, 19 pages.

First Office Action from Chinese Patent Application No. 201410072150.3, dated Apr. 20, 2015, 17 pages.

* cited by examiner

PROCESS ANALYTIC INSTRUMENT WITH MULTI-TUBE CONNECTION

CROSS-REFERENCE TO RELATED APPLICATION

The present application is based on and claims the benefit of U.S. provisional patent application Ser. No. 61/549,427, filed Oct. 20, 2011, the content of which is hereby incorporated by reference in its entirety.

BACKGROUND

Process analytic sensors and instruments are employed in a variety of industries to measure and control gasses and liquids within the process. Process analyzers include, without limitation, process gas chromatographs, process gas analyzers, process hydrocarbon analyzers, continuous emission monitoring systems (CEMS), and the like.

Process analytic instruments, such as gas chromatographs and complex gas and/or liquid analyzers or instruments often require one or more connections to various gases, fluids, air, or vent lines. Installing or servicing such a device requires that these connections be made decoupleable using stainless steel, polymer or other suitable commercially-available industry standard tube fittings. When such instruments have a significant number of tubes or conduits, servicing such tubing/conduits and their associated fittings takes considerable time and skill. Moreover, such service also carries the risk of mis-connection (where a tube is coupled to the wrong port), poor connection where the fitting and/or tube may be damaged or subject to undue stresses that can cause premature failure, or no connection (where the tube is simply not coupled to its required port). Such situations can cause leaks and/or other undesirable results. Further, in the case where hazardous or flammable gases are used, such mis-connections or leaks can also pose a safety hazard.

Process analytic instruments often provide extremely precise measurements relative to process liquids and gasses. As such, it is often necessary to perform periodic maintenance in order to ensure proper function and/calibrations. Providing process analytic instruments that are more easily serviceable and less-prone to human error during servicing would enhance process analytics and thereby facilitate better control of the various processes for which such instruments are used.

SUMMARY

A process analytic instrument includes an analytical module configured to analyze a process fluid and a removable tube carrier coupled to the analytical module. The analytical module has a plurality of inlet ports in a sealing surface. The removable tube carrier has an end with a plurality of apertures aligned with the plurality of inlet ports of sealing surface of the analytical module. The removable tube carrier fluidically couples a plurality of tubes to the analytical module when the end of the removable tube carrier is biased into the sealing surface of the analytical module. A removable tube carrier for coupling to a process analytical module is also provided.

DETAILED DESCRIPTION OF ILLUSTRATIVE EMBODIMENTS

Figure 1:
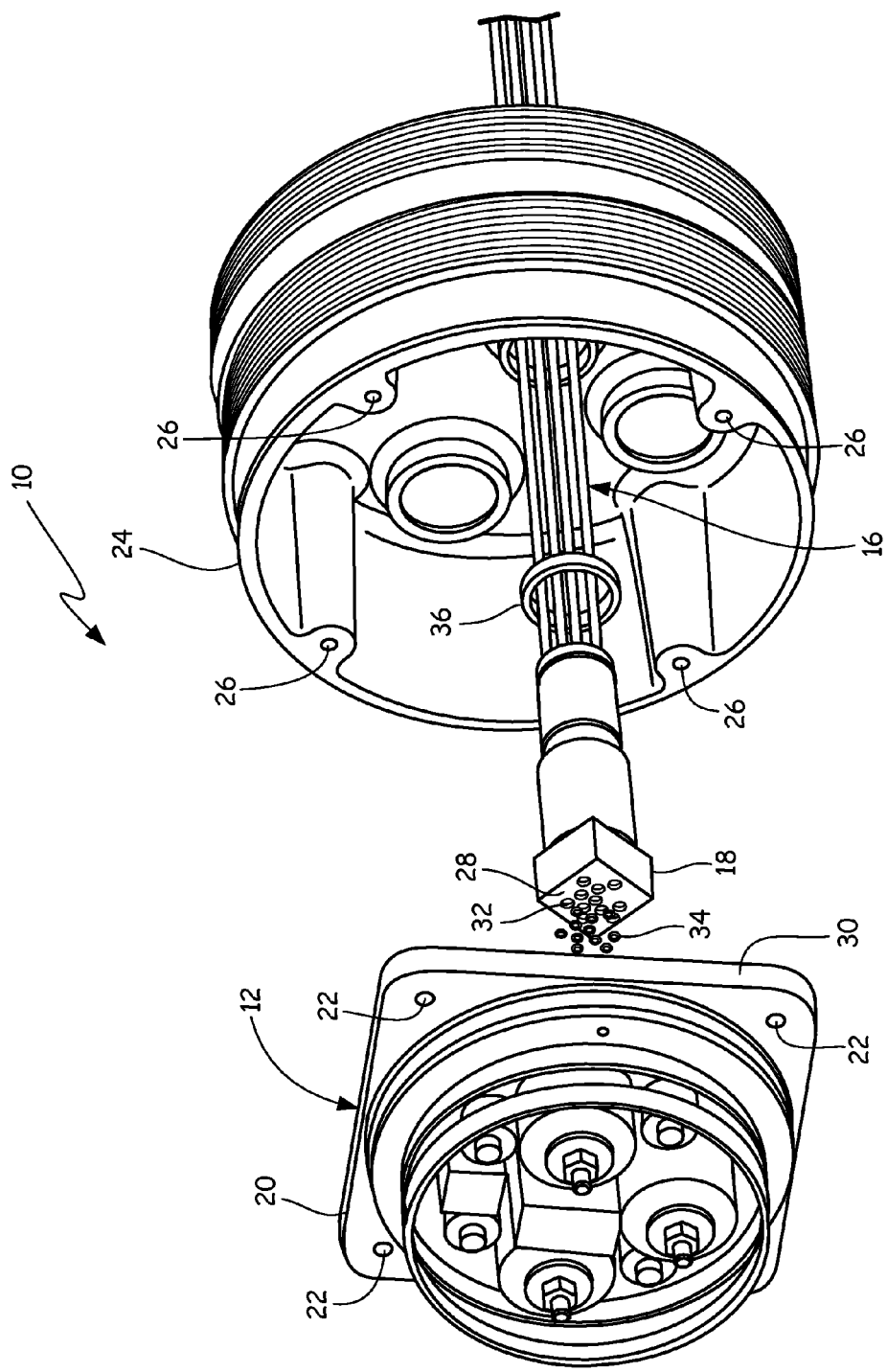
FIG. 1 is a diagrammatic perspective view of a process analytic instrument in accordance with an embodiment of the present invention.

FIG. 1 is a diagrammatic perspective view of a process analytic instrument in accordance with an embodiment of the present invention. Process gas chromatograph (analyzer) 10 includes an analytical module 12 comprising the majority of the chromatographic mechanism for chromatograph 10. As illustrated in FIG. 1, chromatograph 10 has a plurality of tubes or conduits 16 that must be connected between module 12 and analyzer housing 24. In accordance with embodiments of the present invention, the plurality of tubes or conduits 16 are terminated (on at least one end) with modular removable tube carrier 18 that facilitates rapid and secure replacement of chromatographic analytical module 12. Embodiments of the present invention provide for coupling multiple tubes or conduits between analyzer housing 24 and module 12 in a manner that does not use individual tube fittings. Moreover, utilization of modular tube carrier 18 provides for positive sealing of multiple tubes or conduits in assigned or preselected positions such that tubing exchange or mis-assignment is prevented. Embodiments of the present invention thus help consolidate multiple tubes or conduit into a single tube carrier where each tube or conduit has an assigned position in the tube carrier. The individual tubes or conduits are preferably sealed and potted permanently into tube carrier 18. However, embodiments of the present invention can be practiced where the tubes or conduits are fixedly attached within the tube carrier in accordance with any suitable techniques.

Analytical module 12 includes a variety of valves, sensors, conduits and electronics appropriate for its analytical function. For example, an analytical module for a gas chromatograph may include a number of valves, heaters, chromatographic columns, sensors such as a flame ionization detector (FID) and/or thermal conductivity detector (TCD), et cetera. Embodiments where the analytical module serves a different function, such as a process gas oxygen sensor, will have different components suitable for such function. Analytical module 12 includes base plate 20 that has a number of mounting holes 22 that allow base plate 20 to be securely mounted to housing 24 via threaded holes 26. Base plate 20 is of sufficient thickness, based on the material from which it is constructed, such that it does not significantly flex as face 28 of modular tube carrier 18 is urged against sealing surface 30, shown in greater detail in FIG. 3.

As illustrated in FIG. 1, face 28 includes a number of apertures 32 that are fluidically coupled to individual tubes or conduits. While the illustrated embodiment shows face 28 having a rectangular shape, any suitable shape can be used for face 28. Disposed within or adjacent each aperture is a seal, such as an elastomeric o-ring 34. Thus, as face 28 is sufficiently urged against surface 30, seals 34 create individual seals for each tube or conduit to surface 30. This allows all fluidic connections to module 12 to be made substantially simultaneously thereby saving significant technician time. Additionally, since a single tube carrier 18 is coupled to module 12, there is no opportunity to make misconnections. Finally, tube carrier 18 and surface 30 preferably include alignment features that prevent any rotation of tube carrier 18 with respect to surface 30 as tube carrier 18 is brought into proximity with surface 30. Further, it is preferred that the alignment features also be configured such that tube carrier 18 may only be coupled to surface 30 in a single angular orientation. This can prevent tube carrier 18 from being coupled to surface 30 while it is erroneously rotated 90 degrees from the proper orientation.

When base plate 20 is mounted to housing 24 it is important that tube carrier 18 continue to be urged into contact with surface 30 to ensure seal integrity. In one embodiment, such bias is provided by compression spring 36 that bears against a surface in housing 18 and urges tube carrier 18 into contact with surface 30. However, embodiments of the present invention can be practiced where any suitable mechanical arrangement is provided that provides sufficient force on tube carrier 18. Such mechanisms include, without limitation, threaded couplings, clamps, magnets, et cetera. Additionally, when base plate 20 is mounted to analyzer housing 24, analyzer housing 24 substantially surrounds and contains tube carrier 18.

Figure 2:
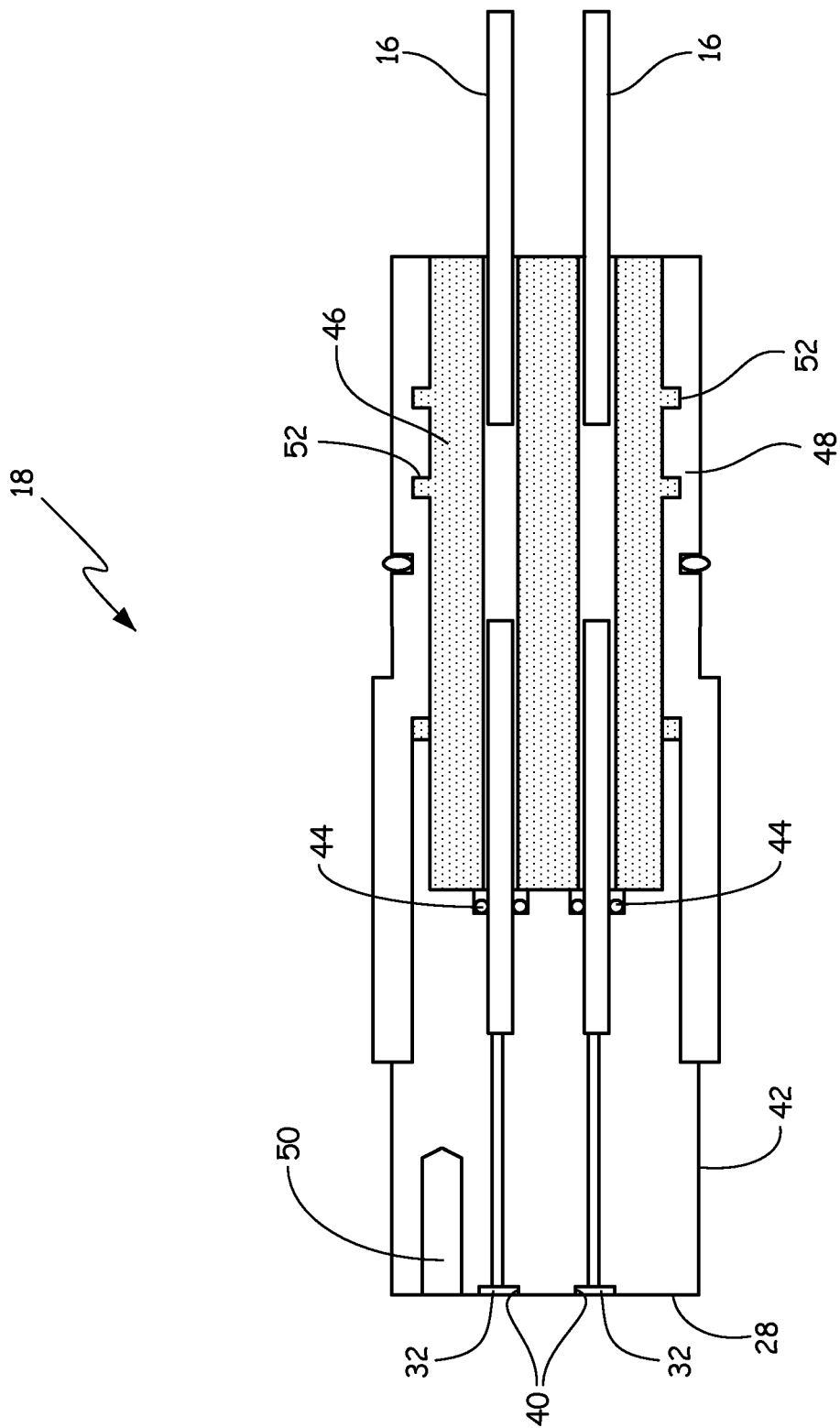
FIG. 2 is a diagrammatic cross-section of a tube carrier in accordance with an embodiment of the present invention.

FIG. 2 is a diagrammatic cross-section of a tube carrier in accordance with an embodiment of the present invention. End 28 of tube carrier 18 provides ports or apertures 32 associated with each tube and includes an axial sealing mechanism, such as an o-ring 34 (shown in FIG. 1), for each port 32. In the embodiment shown in FIG. 2, o-rings 34 are not illustrated; however such o-rings are retained within counterbores 40. Counterbores 40 have diameters that are sized for o-rings 34, and a depth that is less than the thickness of o-rings 34. In this way, o-rings 34 will deform as end 28 is brought into contact with surface 30 of module 12. Tube carrier 18 is placed in analyzer housing 24 in a manner that allows axial translation of tube carrier 18 with respect to housing 24. Analytical module 12 has a mating sealing surface 30 (shown in FIG. 3) with ports or apertures positioned and sized to match ports 32 of tube carrier 18. Installation of module 12 into analyzer housing 24 provides for mating end 28 of tube carrier 18 with surface 30 of module 12 in a single, exact orientation to connect tube ports 32 with associated ports of module 12.

FIG. 2 shows a pair of tubes 16 that are sealingly terminated within tube carrier 18. While FIG. 2 only shows a pair of tubes 16, in fact, any suitable number of tubes may be employed in accordance with embodiments of the present invention. Tubes 16 are fluidically coupled to carrier fitting 42 and such coupling may be facilitated using o-rings 44, which can ensure that potting compound 46 does not leak through fitting 42 when it is injected or poured into fitting shell 48. Further, o-rings 44 can serve the additional purpose of providing a seal against any fluid leaks which might not be contained by potting compound 46. Although o-rings 44 are not relied upon to create the flameproof joint, they may be relied upon for sealing. Fitting 42 preferably includes a plurality of pin alignment holes, one of which is shown at reference numeral 50. These holes 50 cooperate with pins positioned on and extending from surface 30 of module 12 to ensure both that fitting 42 is properly oriented to surface 30 and that fitting 42 does not rotate as surface or end 28 is urged into contact with surface 30. As shown in FIG. 2, shell 48 also includes one or more internal annular grooves 52 that help retain the potting compound or glass frit within shell 48 once the compound or frit has cured or otherwise hardened.

Figure 3:
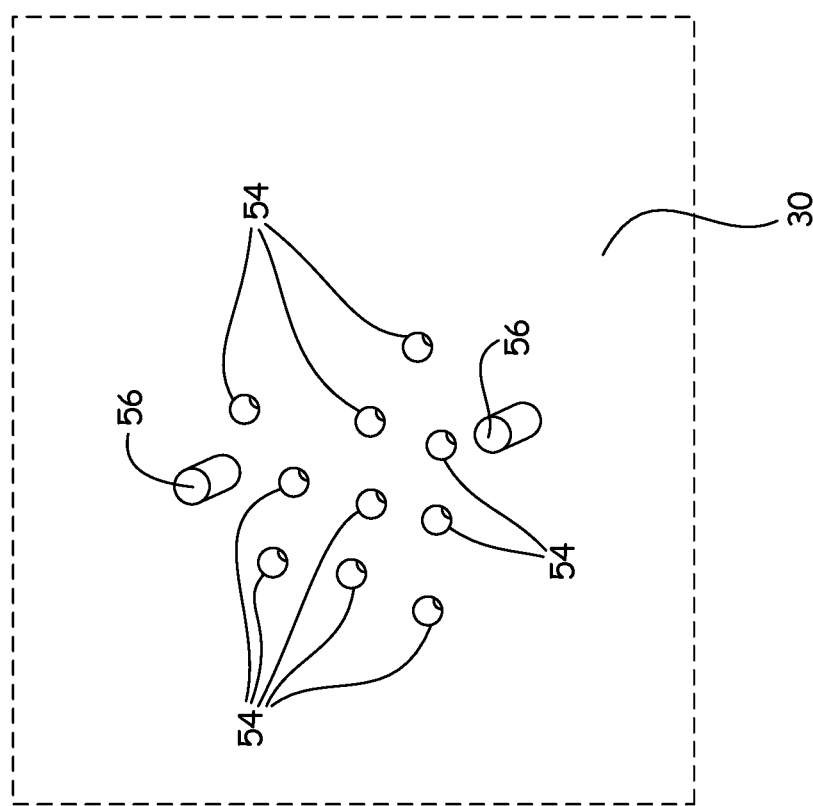
FIG. 3 is a diagrammatic bottom perspective view of a sealing surface of an analytical module in accordance with an embodiment of the present invention.

FIG. 3 is a diagrammatic bottom perspective view of a sealing surface of an analytical module in accordance with an embodiment of the present invention. Surface 30 is shown having ten module ports 54 that are positioned to mate with apertures 32 on end 28 of tube carrier 18. Additionally, two alignment pins 56 are shown, which are received into alignment holes 50 of tube carrier 18 as tube carrier 18 is brought into contact with surface 30. In this way, the resultant assembly allows rapid and positive connection of multiple gas or fluid tubes by means of only the fasteners normally used to position and retain an analyzer module into its housing.

Embodiments of the present invention can also provide for a tube carrier with the above features to provide for a flameproof or explosion-proof connection between two compartments of an analyzer housing. For example, a flame quenching path can be provided between the external diameter of tube carrier 18 and an internal diameter of housing 24 through which it passes, where the path is sized and arranged to provide an agency compliant flame gap which precludes flame propagation but allows free axial translation of tube carrier 18. As above, axial translation of tube carrier 18 is preferably spring loaded to provide a sealing force against module 12 in the installed position. The flame quenching path facilitates compliance with applicable industry-accepted standards from approval agencies such as CSA, UL, FM, ATEX and IEC to provide flame and explosion safe operation. The dimensions of the path and length may be varied based upon design considerations as long as they comply with applicable flameproof standards. Facilitating agency compliance is also made by the use of agency (CSA, UL, FM, ATEX, IEC, et al) compliant potting and materials 46 within shell 48, which materials provide a flameproof seal between analyzer housing 24 and tube carrier 18.

Although the present invention has been described with reference to preferred embodiments, workers skilled in the art will recognize that changes may be made in form and detail without departing from the spirit and scope of the invention.

What is claimed is:

1. A process analytic instrument comprising:
   an analyzer housing;
   an analytical module, coupled to the analyzer housing, configured to analyze a process fluid, the analytical module having a plate with a sealing surface having a plurality of inlet ports;
   a removable tube carrier, contained within the analyzer housing and contained within a space bounded by the analyzer housing and the plate, coupled to the analytical module and having an end with a plurality of apertures aligned with the plurality of inlet ports of the sealing surface of the analytical module, the removable tube carrier fluidically coupling a plurality of tubes to the analytical module when the end of the removable tube carrier is biased into the sealing surface; and
   wherein the plurality of tubes are fixedly terminated within the removeable tube carrier, wherein the removable tube carrier includes a shell surrounding the plurality of tubes and a solid disposed within the shell to mount the plurality of tubes therein; wherein the solid is selected to provide a flame-safe seal, and wherein the solid is a potting compound.

2. The process analytic instrument of claim 1, wherein an external diameter of the removable tube carrier and an internal diameter of the analyzer housing form a flame-quenching pathway.

3. The process analytic instrument of claim 1, and further comprising a spring biasing the removable tube carrier into the sealing surface.

4. The process analytic instrument of claim 1, and further comprising a plurality of seals compressed between the end of the removable tube carrier and the sealing surface, each seal fluidically sealing a respective aperture of the removable tube carrier to a respective inlet port of the analytical module.

5. The process analytic instrument of claim 4, wherein the plurality of seals are o-rings.

6. The process analytic instrument of claim 1, and further comprising at least one alignment feature configured to ensure alignment between the inlet ports and the plurality of apertures as the end of the removable tube carrier is translated axially to the sealing surface.

7. The process analytic instrument of claim 6, wherein the at least one alignment feature is configured to inhibit rotation of the end of the removable tube carrier with respect to the sealing surface as the end of the removable tube carrier is translated axially to the sealing surface.

8. The process analytic instrument of claim 7, wherein the alignment feature includes a plurality of pins extending from one of the sealing surface and the end of the removable tube carrier and a corresponding hole in the other of the sealing surface and the end of the removable tube carrier.

9. The process analytic instrument of claim 1, wherein the shell includes at least one internal annular groove to retain the solid.

10. The process analytic instrument of claim 1, wherein the analytical module is a gas chromatography module.

11. A removable tube carrier for coupling to a process analytical module, the removable tube carrier comprising:
an end having a plurality of apertures disposed to align with a plurality of inlet ports of a sealing surface of the process analytical module;
a plurality of tubes, configured to connect between the process analytical module and an analyzer housing, sealingly terminating within the removable tube carrier; and
wherein biasing the end against the sealing surface of the process analytical module fluidically seals each respective tube to a respective inlet port of the process analytical module.

12. A process analytic module comprising:
a plurality of tubes fixedly connected to a tube carrier and configured to connect between the process analytical module and an analyzer housing;
a plurality of apertures on a face of the process analytical module, wherein each one of the plurality of apertures is configured to fluidically couple to one of each of the plurality of tubes, wherein each of the plurality of apertures and each of the plurality of tubes are fixedly positioned such that each of the plurality of apertures aligns and shares a common axis with a single one of the plurality of tubes, wherein each of the plurality of apertures further comprises an o-ring; and
wherein each of the plurality of tubes is configured such that the alignment is maintained during decoupling and recoupling from the plurality of apertures.

13. The process analytic module of claim 12, and further comprising a plurality of alignment features and wherein the alignment of each of the plurality of tubes is maintained by the plurality of alignment features.

14. A process analytic instrument comprising:
an analyzer housing;
an analytical module, coupled to the analyzer housing, configured to analyze a process fluid, the analytical module having a plate with a sealing surface having a plurality of inlet ports;
a removable tube carrier, contained within the analyzer housing and contained within a space bounded by the analyzer housing and the plate, coupled to the analytical module and having an end with a plurality of apertures aligned with the plurality of inlet ports of the sealing surface of the analytical module, the removable tube carrier fluidically coupling a plurality of tubes to the analytical module when the end of the removable tube carrier is biased into the sealing surface, wherein the end of the removable tube carrier is rectangular.

* * * * *